(12) United States Patent
Naessén

(10) Patent No.: US 8,556,817 B2
(45) Date of Patent: Oct. 15, 2013

(54) NON-INVASIVE METHODS FOR DETERMINING THE CARDIOVASCULAR STATUS OF AN INDIVIDUAL

(76) Inventor: Tord Naessén, Uppsala (SE)

( * ) Notice: Subject to any disclaimer, the term of this patent is extended or adjusted under 35 U.S.C. 154(b) by 976 days.

(21) Appl. No.: 11/887,560

(22) PCT Filed: Apr. 3, 2006

(86) PCT No.: PCT/IB2006/001691
§ 371 (c)(1),
(2), (4) Date: Oct. 1, 2007

(87) PCT Pub. No.: WO2006/136928
PCT Pub. Date: Dec. 28, 2006

(65) Prior Publication Data
US 2008/0167559 A1    Jul. 10, 2008

Related U.S. Application Data

(60) Provisional application No. 60/668,150, filed on Apr. 4, 2005.

(51) Int. Cl.
*A61B 8/08* (2006.01)

(52) U.S. Cl.
USPC ........... 600/449; 600/437; 600/438; 600/443; 128/898

(58) Field of Classification Search
USPC ......... 600/437, 438, 467, 410, 411, 425, 527; 382/128
See application file for complete search history.

(56) References Cited

PUBLICATIONS

O'Leary, Daniel et al. Carotid-Artery Intima and Media Thickness As a Risk Factor for Myocardial Infarction and Stroke in Older Adults. The New England Journal of Medicine. 340:14-22. Jan. 7, 1999.*
Sator et al, Maturitas, 30:63-68 (1998).
Baron et al, Obstetrics & Gynecology, 91(6):982-986 (1998).
Baron et al, Maturitas, 27:47-53 (1997).
Writing Group for the Women's Health Initiative Investigators, Risks and Benefits of Estrogen and Progestin in Healthy Postmenopausal Women, JAMA, 288(3):321-333 (2002).

* cited by examiner

*Primary Examiner* — Parikha Mehta
(74) *Attorney, Agent, or Firm* — Porter Wright Morris & Arthur, LLP

(57) ABSTRACT

Non-invasive methods for determining the cardiovascular status of an individual comprising measuring the thickness of the artery intima layer and/or the artery media layer and determining the cardiovascular status of the individual based on the thickness of the intima layer and/or the intima to media (I/M) thickness ratio are provided.

21 Claims, 6 Drawing Sheets

Common carotid artery intima thickness (mm), media thickness and intima/media thickness ratio in groups of women with regard to different mean age, long-term estrogen therapy and 70-year old women with different types of cardiovascular diseases.

Common carotid artery intima thickness (mm), media thickness and intima/media thickness ratio in groups of women with regard to different mean age, long-term estrogen therapy and 70-year old women with different types of cardiovascular diseases.

Carotid Artery Intima, Media and I/M ratio by Study Group and 70-yr old women with no CVD

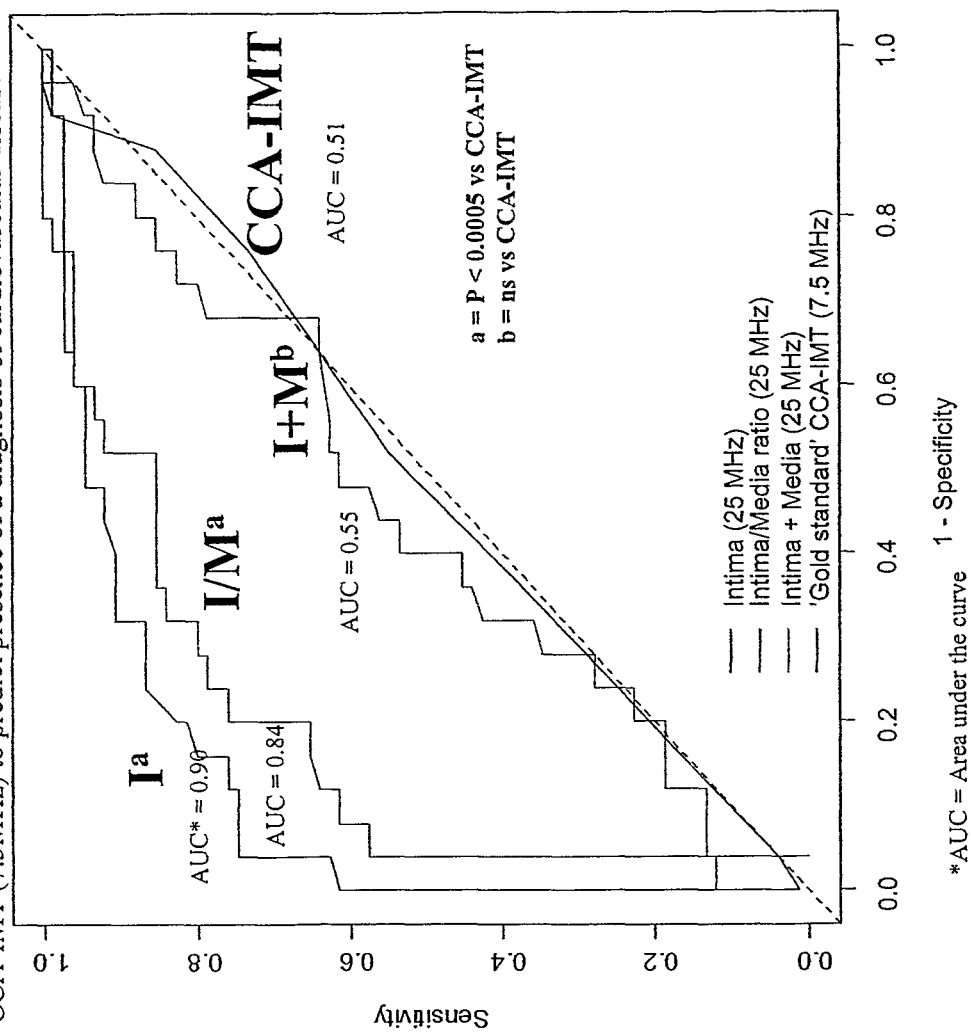
Fig. 5 Receiver Operating Characteristic (ROC) plots for the use of carotid artery intima thickness, intima/media thickness ratio, the combined intima+media thickness (all with 25MHz) and conventional CCA-IMT (7.5MHz) to predict presence of a diagnosis of cardiovascular disease

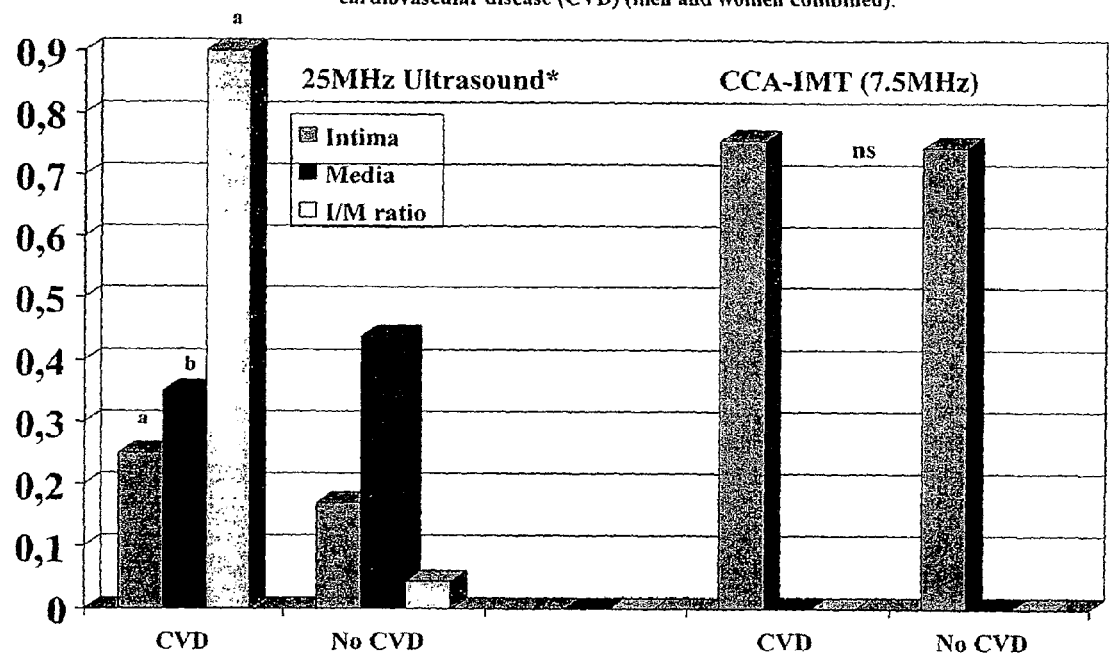
Figure 6 – Common carotid artery intima thickness (mm), media thickness and intima/media thickness ratio assessed by high-frequency ultrasound and conventional carotid CMT (7.5 MHz) in 70-year old individuals with and without a diagnosis of cardiovascular disease (CVD) (men and women combined).
a = P < 0.001, compared with no CVD
b = P < 0.05
* Based on data from ref. xx, with permission

NON-INVASIVE METHODS FOR DETERMINING THE CARDIOVASCULAR STATUS OF AN INDIVIDUAL

RELATED APPLICATION

This application is a 371 of PCT/IB2006/001691 filed Apr. 3, 2006 which claims priority under 35 U.S.C. §119 of U.S. Provisional Application Ser. No. 60/668,150 filed Apr. 4, 2005.

FIELD OF THE INVENTION

The present invention relates to non-invasive methods for determining the cardiovascular status of an individual comprising measuring the thickness of an artery intima layer and optionally the thickness of an artery media layer in the individual and determining the cardiovascular status of the individual based on the thickness of the intima layer and/or the intima to media (I/M) thickness ratio. Non-invasive methods for diagnosing a cardiovascular disease and methods for monitoring a change in the cardiovascular status of an individual are also provided.

BACKGROUND OF THE INVENTION

The "Gold standard" for non-invasively determining the artery wall condition in an individual is by measuring the Intima-Media Thickness (IMT) complex using 7-8 MHz ultrasound. However, with increasing age and development of atherosclerosis, the intima and media layers change in different directions, i.e. the intima increases and the media becomes thinner. These different changes in the artery wall layers cannot be properly imaged by using the conventional 7-8 MHz ultrasound mainly because of limited resolution due to low frequency. In addition, when using 7-8 MHz ultrasound probes, the far wall of the artery has to be used for measuring the IMT complex and therefore, the order and interference of preceding artery wall layers on the ultrasound signal affects the measurement estimates.

SUMMARY OF THE INVENTION

The present invention provides non-invasive methods for determining a cardiovascular status of an individual. In one embodiment, the methods comprise: (a) measuring a thickness of an artery intima layer in the individual and (b) determining the cardiovascular status of the individual based on the thickness of the intima layer. In another embodiment, the methods comprise: (a) measuring a thickness of an artery intima layer in the individual; (b) measuring a thickness of an artery media layer in the individual; and (c) determining the cardiovascular status of the individual based on the intima to media (I/M) thickness ratio.

The present invention also provides non-invasive methods for diagnosing a cardiovascular disease in an individual. In one embodiment, the methods comprise: (a) measuring a thickness of an artery intima layer in the individual and (b) diagnosing whether the individual has or is at risk of developing a cardiovascular disease based on the thickness of the intima layer. In another embodiment, the methods comprise: (a) measuring a thickness of an artery intima layer in the individual; (b) measuring a thickness of an artery media layer in the individual; and (c) diagnosing whether the individual has or is at risk of developing a cardiovascular disease based on the intima to media (I/M) thickness ratio.

The present invention further provides non-invasive methods for monitoring a change in a cardiovascular status of an individual. In one embodiment, the methods comprise: (a) measuring a thickness of an artery intima layer in the individual and (b) determining whether there is a change in the cardiovascular status of the individual based on the thickness of an artery intima layer. In another embodiment, the methods comprise: (a) measuring a thickness of an artery intima layer in the individual; (b) measuring a thickness of the artery media layer in the individual; and (c) determining whether there is a change in the cardiovascular status of the individual based on the intima to media (I/M) thickness ratio.

DETAILED DESCRIPTION OF THE FIGURES

The description of the invention will be more fully understood in view of the figures, in which.

FIG. 5 is a graph depicting Receiver Operating Characteristic (ROC) plots for the use of carotid artery intima thickness, intima to media thickness ration, the combined intima+media thickness (all with 25 MHz) and conventional CCA-IMT (7.5 MHz) to predict presence of a cardiovascular disease; and FIG. 6 is a bar diagram comparing mean values in 70-year old individuals with and without a diagnosis of cardiovascular disease (CVD) when using high-frequency ultrasound and the conventional carotid-IMT (7.5 MHz).

DETAILED DESCRIPTION OF THE INVENTION

Figure 1:
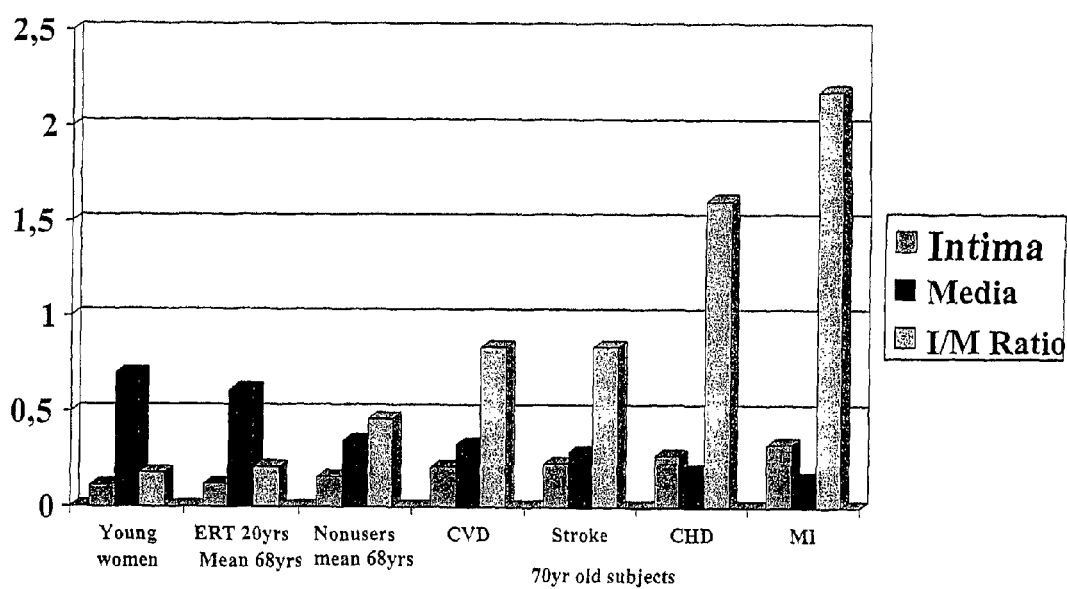
FIG. 1 is a bar diagram depicting the carotid artery intima thickness, the carotid artery media layer thickness and the intima to media (I/M) thickness ratio in groups of women with regard to different mean age, long-term estrogen therapy and 70-year old women with different types of cardiovascular diseases.
Figure 2:
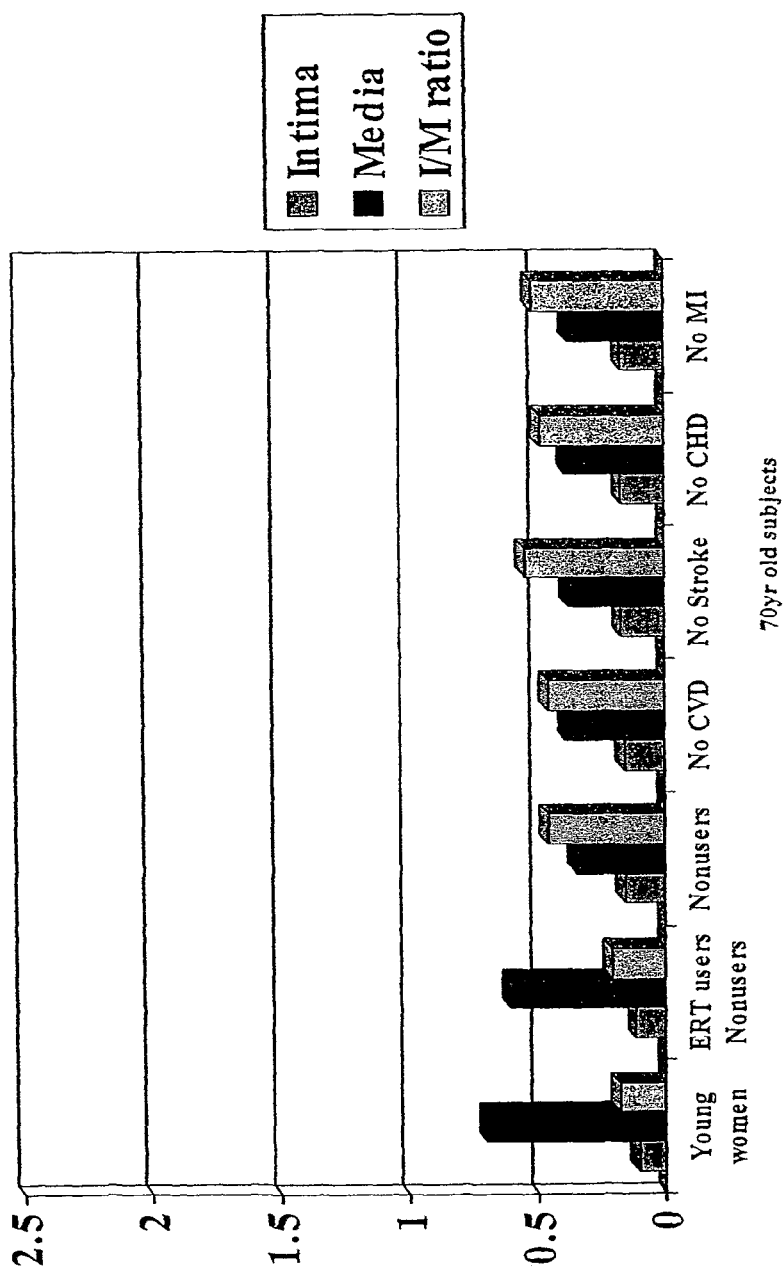
FIG. 2 is a bar diagram depicting the carotid artery intima thickness, the carotid artery media layer thickness and the intima to media (I/M) thickness ratio by study group and 70-year old women without a diagnosis of cardiovascular disease.

The inventor has determined that separate measurements of the thickness of an artery intima layer and optionally an artery media layer and the use of the intima layer thickness or the intima to media (I/M) thickness ratio provide valuable information regarding the cardiovascular status of an individual. With increasing age and the development or presence of a cardiovascular disease, the intima and media layers change in different directions, i.e. the artery intima layer increases and the artery media layer becomes thinner and thus, the intima to media (I/M) thickness ratio increases. Tables 1 and 2 and FIGS. 1 and 2 illustrate the differences in the thickness of the artery intima layer and the artery media layer in different groups of individuals studied with regard to age, estrogen exposure in women and presence/absence of a diagnosis of a cardiovascular disease. These differences cannot be properly imaged/monitored by the conventional technique for measuring the IMT discussed above. The Tables, specifically Table 3, FIG. 5, and FIG. 6 illustrate the usefulness and superiority of separate estimates of the artery intima layer, the artery media layer and the intima to media thickness ration over the conventional method of measuring the IMT. Because the conventional IMT assessment includes both the artery intima layer and the artery media layer in one single measurement, and since these layers change in differential directions with, for example, increasing age and atherosclerosis, the utility of the IMT approach for estimation of artery wall condition and prediction of future risk of cardiovascular disease is limited. Accordingly, the inventor has determined that measuring the artery wall layers, i.e., the artery intima layer and the artery media layers, separately can thereby more accurately determine the cardiovascular status of the artery walls of an individual. Separate measurements of the thickness of the artery intima and/or media layers and the use of the intima to media (I/M) thickness ratio is therefore preferable to the conventional non-invasive technique of measuring the IMT complex in one single measurement.

Tables 1-3:

TABLE 1

Thickness of the carotid and femoral artery total wall, media and intima layers (mm) and Intima/Media thickness ratio in the study groups.

| Variable | Postmenopausal Estrogen users (n = 17) | Postmenopausal Age-matched Nonusers (n = 17) | Mean difference ± SD (95% CI) | % difference P* | Premenopausal Women (n = 20) |
|---|---|---|---|---|---|
| Carotid artery | | | | | |
| Total wall thickness | $0.84 \pm 0.19$ | $0.62 \pm 0.14^c$ | $0.23 \pm 0.23$ (0.11, 0.34) | +35% $0.0008^e$ | $0.92 \pm 0.26$ |
| Media thickness | $0.61 \pm 0.19$ | $0.35 \pm 0.11^c$ | $0.26 \pm 0.22$ (0.14, 0.37) | +74% $0.0002^{d,e}$ | $0.70 \pm 0.24$ |
| Intima thickness | $0.12 \pm 0.02$ | $0.16 \pm 0.04^c$ | $-0.033 \pm 0.04$ (−0.05, −0.01) | −25% $0.0002^{d,e}$ | $0.11 \pm 0.02$ |
| Intima/Media ratio | $0.21 \pm 0.0629^a$ | $0.46 \pm 0.13^c$ | $-0.25 \pm 0.15$ (−0.17, −0.33) | −54% $<0.0001^{d,e}$ | $0.18 \pm 0.05$ |
| Thickness of Intima + Media | $0.73 \pm 0.19$ | $0.51 \pm 0.13^c$ | $0.22 \pm 0.23$ (0.10, 0.34) | +43% 0.001 | $0.81 \pm 0.24$ |
| Femoral artery | | | | | |
| Total wall thickness | $0.91 \pm 0.37^b$ | $0.73 \pm 0.28^c$ | $0.18 \pm 0.40$ (−0.02, 0.38) | +25% 0.08 | $1.23 \pm 0.33$ |
| Media thickness | $0.77 \pm 0.29^a$ | $0.51 \pm 0.23^c$ | $0.27 \pm 0.30$ (0.10, 0.42) | +51% <0.003 | $0.99 \pm 0.32$ |
| Intima thickness | $0.095 \pm 0.02$ | $0.124 \pm 0.04^b$ | $-0.030 \pm 0.04$ (−0.05, −0.01) | −23% $0.01^{d,e}$ | $0.095 \pm 0.02$ |
| Intima/Media ratio | $0.14 \pm 0.06^{0.055}$ | $0.28 \pm 0.13^c$ | $-0.14 \pm 0.13$ (−0.21, −0.08) | −50% $0.0003^{d,e}$ | $0.10 \pm 0.03$ |
| Thickness of Intima + Media | $0.87 \pm 0.30^a$ | $0.63 \pm 0.25^c$ | $0.24 \pm 0.33$ (0.07, 0.40) | +38% 0.008 | $1.10 \pm 0.32$ |

Data are presented as mean ± SD.
*Test of pair-wise differences between postmenopausal estrogen users and nonusers.
$^a$P < 0.05,
$^b$P < 0.01,
$^c$P < 0.0001 when compared with premenopausal women.
$^d$Remained significant after adjustment for differences in systolic blood pressure, diastolic blood pressure and body mass index.
$^e$Remained significant after exclusion of hypertensive subjects.

TABLE 2

Carotid total artery wall, media thickness, intima thickness and intima/media (I/M) ratio estimated by high-frequency ultrasound by presence and type of CVD when compared with healthy subjects with no CVD (n = 61). Subjects with diabetes and hyperlipidemia were compared with subjects without those disorders

| | total wall mean ± SD | P | media mean ± SD | P | intima mean ± SD | P | I/M ratio mean ± SD | % difference# | P | I + M mean ± SD | P |
|---|---|---|---|---|---|---|---|---|---|---|---|
| All CVD* | | 0.4 | | <0.05 | | <0.0001 | | +74% | <0.0005 | | 0.51 |
| Yes n = 39 | 0.72 ± 0.20 | | 0.38 ± 0.16 | | 0.22 ± 0.06 | | 0.75 ± 0.48 | | | 0.60 ± 0.15 | |
| No n = 61 | 0.75 ± 0.17 | | 0.45 ± 0.14 | | 0.17 ± 0.06 | | 0.43 ± 0.20 | | | 0.62 ± 0.15 | |
| CHD† | | 0.1 | | <0.001 | | <0.0001 | | +163% | <0.0001 | | 0.12 |
| Yes n = 11 | 0.64 ± 0.22 | | 0.28 ± 0.12 | | 0.26 ± 0.05 | | 1.13 ± 0.62 | | | 0.54 ± 0.11 | |
| No CVD n = 61 | 0.75 ± 0.17 | | 0.45 ± 0.14 | | 0.17 ± 0.06 | | 0.43 ± 0.20 | | | 0.62 ± 0.15 | |
| MI‡ | | 0.7 | | <0.005 | | <0.0001 | | +195% | <0.0005 | | 0.19 |
| Yes n = 7 | 0.72 ± 0.15 | | 0.26 ± 0.12 | | 0.27 ± 0.06 | | 1.27 ± 0.71 | | | 0.54 ± 0.10 | |
| No CVD n = 61 | 0.75 ± 0.17 | | 0.45 ± 0.14 | | 0.17 ± 0.06 | | 0.43 ± 0.20 | | | 0.62 ± 0.15 | |
| Stroke | | 0.9 | | <0.05 | | <0.0001 | | +88% | <0.0001 | | 0.65 |
| Yes n = 17 | 0.75 ± 0.20 | | 0.37 ± 0.19 | | 0.25 ± 0.04 | | 0.81 ± 0.35 | | | 0.61 ± 0.19 | |
| No CVD n = 61 | 0.75 ± 0.17 | | 0.45 ± 0.14 | | 0.17 ± 0.06 | | 0.43 ± 0.20 | | | 0.62 ± 0.15 | |
| Hypertension | | 0.7 | | 0.3 | | <0.0005 | | +44% | <0.05 | | 0.85 |
| Yes n = 30 | 0.73 ± 0.22 | | 0.41 ± 0.16 | | 0.22 ± 0.06 | | 0.62 ± 0.34 | | | 0.63 ± 0.15 | |
| No CVD n = 61 | 0.75 ± 0.17 | | 0.45 ± 0.14 | | 0.17 ± 0.06 | | 0.43 ± 0.20 | | | 0.62 ± 0.15 | |
| Diabetes | | 0.5 | | 0.1 | | 0.1 | | +37% | 0.1 | | 0.34 |
| Yes n = 7 | 0.69 ± 0.16 | | 0.33 ± 0.11 | | 0.22 ± 0.05 | | 0.74 ± 0.34 | | | 0.55 ± 0.09 | |

TABLE 2-continued

Carotid total artery wall, media thickness, intima thickness and intima/media (I/M) ratio estimated by high-frequency ultrasound by presence and type of CVD when compared with healthy subjects with no CVD (n = 61). Subjects with diabetes and hyperlipidemia were compared with subjects without those disorders

| | total wall mean ± SD | P | media mean ± SD | P | intima mean ± SD | P | I/M ratio mean ± SD | % difference# | P | I + M mean ± SD | P |
|---|---|---|---|---|---|---|---|---|---|---|---|
| No n = 93 | 0.74 ± 0.19 | | 0.43 ± 0.16 | | 0.19 ± 0.06 | | 0.54 ± 0.37 | | | 0.62 ± 0.15 | |
| Hyperlipidemia | | 0.5 | | 0.1 | | <0.0005 | | +70% | <0.01 | | 0.97 |
| Yes§ n = 21 | 0.76 ± 0.20 | | 0.38 ± 0.18 | | 0.24 ± 0.07 | | 0.82 ± 0.58 | | | 0.62 ± 0.17 | |
| No n = 79 | 0.73 ± 0.18 | | 0.43 ± 0.15 | | 0.18 ± 0.06 | | 0.48 ± 0.26 | | | 0.61 ± 0.15 | |

*All CVD: All cardiovascular diseases combined including coronary heart disease (CHD), heart failure, stroke and hypertension.
†CHD: including myocardial infarction, angina pectoris, coronary by-pass or balloon angioplasty
‡MI: myocardial infarction
§Including subjects treated with lipid lowering medications
Percentage difference from mean values in healthy subjects

TABLE 3

Receiver Operative Curve (ROC) analyses illustrating the usefulness of separate estimates of carotid artery intima layer and intima/media thickness ratio, using high-frequency (25 MHz) ultrasound, to predict varying types of cardiovascular diseases (CVD) and risk factors for CVD. For comparison corresponding values for conventional carotid artery IMT (7.5 MHz) and estimates using 25 MHz ultrasound (intima + media thickness and thickness of carotid total wall) that most closely correspond to IMT, are given.

| | IMTdx 7.5 MHz mean ± SD | ROC Intima P AUC# | ROC Int/Med P AUC | ROC Int + Med P AUC | ROC Total wall P AUC | ROC IMTdx 7.5 MHz P AUC |
|---|---|---|---|---|---|---|
| All CVD* | | 0.0003 | 0.0002 | 0.59 | 0.34 | 0.35 |
| Yes n = 39 | 0.77 ± 0.16 | 0.77 | 0.72 | 0.54 | 0.55 | 0.55 |
| No n = 61 | 0.74 ± 0.16 | | | | | |
| All CVD excl. HT | | <0.0001 | <0.0001 | 0.61 | 0.50 | 0.77 |
| Yes n = 25 | | 0.90 | 0.84 | 0.55 | 0.54 | 0.51 |
| No n = 75 | | | | | | |
| CHD† | | 0.0023 | 0.0002 | 0.11 | 0.08 | 0.72 |
| Yes n = 11 | | 0.92 | 0.92 | 0.65 | 0.64 | 0.50 |
| No CVD n = 61 | | | | | | |
| MI‡ | | 0.0054 | 0.002 | 0.17 | 0.66 | 0.65 |
| Yes n = 7 | | 0.95 | 0.94 | 0.66 | 0.55 | 0.53 |
| No CVD n = 61 | | | | | | |
| Stroke | | 0.0004 | 0.0001 | 0.90 | 0.97 | 0.38 |
| Yes n = 17 | | 0.89 | 0.83 | 0.54 | 0.52 | 0.55 |
| No CVD n = 61 | | | | | | |
| Hypertension | | 0.0034 | 0.0035 | 0.79 | 0.56 | 0.22 |
| Yes n = 30 | | 0.73 | 0.66 | 0.51 | 0.63 | 0.58 |
| No CVD n = 61 | | | | | | |
| Hyperlipidemia | | 0.0007 | 0.0011 | 0.96 | 0.76 | 0.68 |
| Yes§ n = 21 | | 0.81 | 0.73 | 0.49 | 0.51 | 0.54 |
| No n = (79)/69 | | | | | | |

*All CVD: All cardiovascular diseases combined including coronary heart disease (CHD), heart failure, stroke and hypertension (HT).
†CHD: including myocardial infarction, angina pectoris, coronary by-pass or ballon angioplasty
‡MI: myocardial infarction
§Including subjects treated with lipid lowering medications
Area Under the Curve In one embodiment, the present invention is directed to non-invasive methods for determining the cardiovascular status of an individual. In one embodiment, the methods comprise: (a) measuring a thickness of an artery intima layer in the individual and (b) determining the cardiovascular status of the individual based on the thickness of the intima layer. In another embodiment, the methods comprise: (a) measuring a thickness of an artery intima layer in the individual; (b) measuring a thickness of an artery media layer in the individual; and (c) determining the cardiovascular status of the individual based on the intima to media (I/M) thickness ratio.

As used herein, "cardiovascular status" refers to the physiological status of the cardiovascular system as reflected in thickness of the artery intima layer, the artery media layer and/or the intima to media (I/M) thickness ratio. Also included in the cardiovascular status are changes in the thickness of the artery intima layer, the artery media layer, and/or the intima to media (I/M) thickness ratio. The cardiovascular status of an individual may be deranged and changed in the negative direction by, for example, aging and specific diseases/conditions or risk factors, or in the positive direction by, for example, medications and intervention therapies, including medical intervention therapies, pharmacological intervention therapies and lifestyle changes, such as diet, physical activity, cessation or commencement of smoking and/or stress reduction, etc. As such, the cardiovascular status is a continuous and sometimes progressive process that may end up in a diagnosed disease, such as cardiovascular-related diseases or symptoms specific for a deranged artery system. Symptoms of a deranged artery system include, but are not limited to, angina pectoris, claudicatio intermittens, etc. Cardiovascular-related diseases include, but are not limited to, hypertension, acute myocardial infarction, silent myocardial infarction, stroke, angina, coronary heart disease and atherosclerosis.

Figure 3:
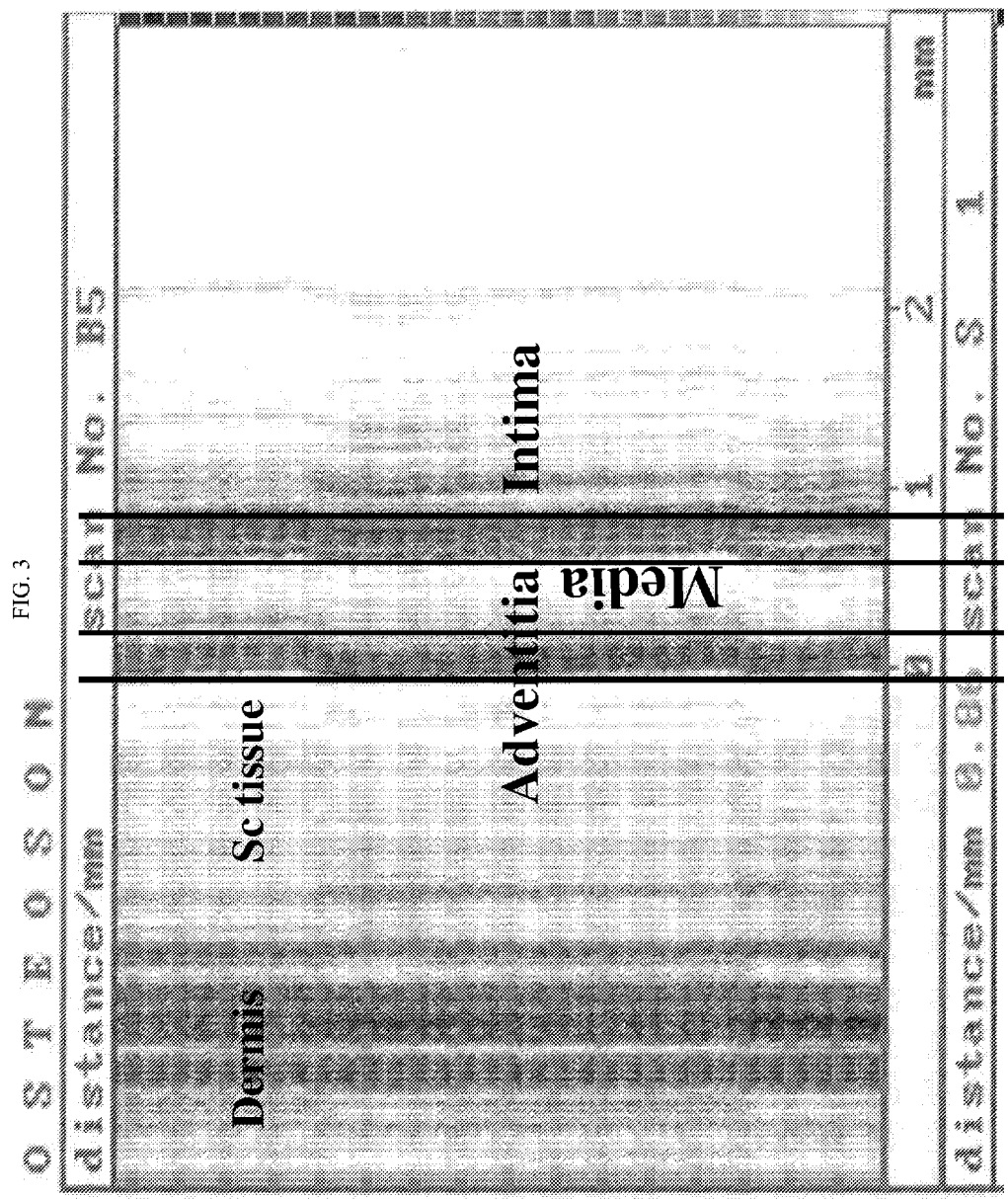
FIG. 3 is an ultrasound image (25 MHz) of an artery depicting the artery intima layer, the artery media layer and the artery adventitia layer.

As schematically illustrated in FIG. 3, an artery comprises three layers: the artery intima layer, the artery media layer and the artery adventitia layer. The artery intima layer is comprised of mainly epithelial cells and is in direct contact with the flow of blood. The artery media layer is outside the artery intima layer and is comprised mainly of smooth muscle cells and elastic tissue. The outermost layer of the artery is the artery adventitia layer, which is mainly comprised of connective tissue.

Figure 4:
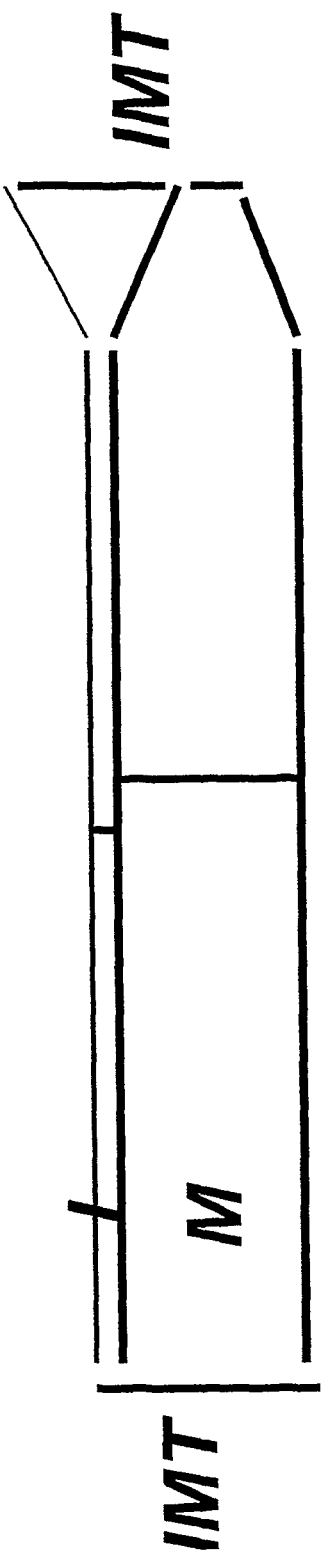
FIG. 4 is a schematic illustration of the artery intima layer, the artery media layer and the IMT complex and changes in thickness of the artery intima layer and the artery media layer with aging and development of atherosclerosis.

As shown in FIG. 4, the conventional method for determining the cardiovascular status of an individual is to measure the entire intima-media thickness (IMT) complex in one single measurement using an ultrasound frequency of 7-8 MHz. However, because the artery intima layer and the artery media layer may change in different directions, e.g., the intima increases and the media becomes thinner as seen in aging and cardiovascular related disease, the inventor has found that separate measurements of the artery intima layer and the artery media layer and the use of the intima to media (I/M) thickness ratio more accurately determines the cardiovascular status of the individual, In the present invention, the thickness of an artery intima layer and/or an artery media layer is non-invasively measured in an individual to determine the cardiovascular status of the individual. One skilled in the art will appreciate the various non-invasive methods for measuring the thickness of the artery intima layer and/or the artery media layer, any of which may be employed herein. Non-invasive methods for measuring the thickness of the artery intima layer and/or the artery media layer include, but are not limited to, ultrasound, backscatter ultrasound, magnetic resonance (MR), duplex ultrasound, computed tomography (CT), including multi-detector row CT, or a combination thereof. When using an ultrasound source, the inventor has determined that a frequency higher than the conventional of 7-8 MHz made it possible to estimate the artery wall layers separately. This high frequency improves the results obtained because the near wall of the artery may be used, eliminating interference from preceding artery wall layers. However, the present invention is not limited to measuring the thickness of the artery intima and/or the artery media layer on the near wall of the artery. With the use of higher frequencies, the far artery wall may also be used. In one embodiment, the ultrasound frequency is greater than 15 MHz. In another embodiment, the ultrasound frequency is greater than 20 MHz. In a further embodiment, the ultrasound frequency is about 25 MHz. The frequency of the ultrasound source may be transmitted with a broad-band or single-band probe.

Any artery within the focus depth of the selected measuring equipment that can give information of the separate thicknesses of the artery intima layer and optionally the artery media layer may be used. In one embodiment, the thickness of the artery intima layer and optionally the artery media layer is measured in a superficial artery. Examples of superficial arteries include, but are not limited to, carotid, femoral, radialis, cubital, temporal, popliteal, or dorsalis pedis arteries. Depending on the artery which is selected for measurement, one skilled in the art will appreciate the various non-invasive locations on the individual in which the artery layer thickness may be measured. In one embodiment, the artery is a carotid artery and is examined in front of the sternocleidomastoid muscle, with the individual in the sitting position. In another embodiment, the artery is a femoral artery and is examined below the inguinal ligament, midway between the anterior superior iliac spine and the symphysis pubis, with the individual in the supine position.

More than one measurement of the artery intima layer and/or the artery media layer may be taken to determine the cardiovascular status of an individual. In one embodiment, at least 10 consecutive measurements of the thickness of the artery intima layer and/or the artery media layer are obtained in place or along the length of the selected artery. If multiple measurements are taken, the mean value of such measurements may be calculated and used to determine the cardiovascular status of the individual. These multiple measurements may be taken in a single location of the artery or may be taken along a length of the artery. In one embodiment, the measurements are taken around a 0.5-1 cm length of an artery. If measurements are taken along a distance of an artery, an ultrasound sensor head covering a corresponding length (linear probe) may be used to facilitate such measurements.

In another embodiment of the invention, non-invasive methods for diagnosing a cardiovascular disease in an individual are also provided. In, one embodiment, the methods comprise (a) measuring a thickness of an artery intima layer in the individual and (b) diagnosing whether the individual has or is at risk of developing a cardiovascular disease based on the thickness of the intima layer. In another embodiment, the methods comprise: (a) measuring a thickness of an artery intima layer in the individual; (b) measuring a thickness of an artery media layer in the individual; and (c) diagnosing whether the individual has or is at risk of developing a cardiovascular disease based on the intima to media (I/M) thickness ratio.

As used herein, "diagnosing" includes assessing and/or estimating whether the individual has or is at risk of developing a cardiovascular disease based on the thickness of the artery intima layer and/or the intima to media (IM) thickness ratio. In general, as measured at the carotid artery of healthy premenopausal women, the artery intima thickness is about 0.10-0.11 mm and the intima to media (I/M) thickness ratio is about 0.18, Table 1. Corresponding values in 70-year old healthy individuals are about 0.17 mm and 0.43, Table 2. These values differ slightly when women and men, about 70-year old, are analyzed separately, Tables 6-7. Increasing deviations from these values indicate either an increase in the risk of developing a cardiovascular disease or the progression of a cardiovascular disease. The inventor has determined that the likelihood, as measured in 70-year old individuals, of having an abnormal cardiovascular status and thereby having a cardiovascular disease are high with an intima thickness about or greater than 0.19 mm and/or an intima to media (I/M) thickness ratio about or greater than 0.52 mm. However, it is noted that individuals with values just under these values also probably have deranged arteries and are at an increased risk of having a cardiovascular-related disease but have not yet experienced an event, e.g., myocardial infarction or stroke, and therefore, have not received a cardiovascular-related disease diagnosis.

The guidelines given for evaluation of estimates, as depicted in Tables 1-7 and FIGS. 1, 2, 5 and 6, of the artery wall status for an individual are based on mean values for the thickness of the artery intima layer, the thickness of the artery media layer and the intima to media thickness ratio for groups of individuals with regard to age, sex, and presence/absence of a diagnosis of a cardiovascular disease. In addition, the suggested cut-off levels are based on data underlying the ROC analysis (FIG. 6) with optimization of sensitivity and specificity for these 70-year old individuals. Accordingly, the present invention is not limited or defined by such values. While not wishing to be bound by theory, the inventor believes that the cut-off level values, noted above and in the Tables and Figures, for intima thickness and/or intima to media thickness ratio for healthy individuals and individuals having abnormal cardiovascular status will be modified and further improved after additional study.

The present invention is also directed to non-invasive methods for monitoring a change in the cardiovascular status of an individual. In one embodiment, the methods comprise: (a) measuring a thickness of an artery intima layer in the individual and (b) determining the cardiovascular status of the individual based on the thickness of the artery intima layer. In another embodiment, the methods comprise: (a) measuring a thickness of an artery intima layer in the individual; (b) measuring a thickness of an artery media layer in the individual; and (c) determining whether there is a change in the cardiovascular status of the individual based on the intima to media (I/M) thickness ratio.

One skilled in the art will appreciate the various reasons for monitoring the cardiovascular status of an individual. In one embodiment, the methods may be used to evaluate effects of interventions aimed to prevent and/or treat changes in the artery wall, as exemplified by effects of long-term estrogen therapy (Table 1 and the first three groups in FIG. 1). The changes in the cardiovascular status of an individual may also be monitored to access the efficacy of an intervention therapy aimed to treat and/or reduce the risk of developing a condition that effects the artery walls of an individual. Examples of intervention therapy include but are not limited to administration of active agents affecting the structure of the intima layer or the connective tissue and/or muscle elements in the artery media layer or the inflammation process connected with atherosclerosis. In one embodiment, the present methods are used for monitoring effects of interventions against arterial aging and atherosclerosis. In another embodiment, the present methods are used for monitoring effects of medical intervention, pharmacological intervention, and lifestyle changes such as diet, physical activity, the cessation or commencement of smoking, stress reduction, or a combination thereof.

In another embodiment, the cardiovascular status of an individual is monitored in premenopausal women to observe the effects, inter alia, anovulation, hormonal disturbances such as Polycystic Ovary Syndrome, hyperlipidemia and/or Metabolic Syndrome, the effects of oral contraceptives, or the like. In yet another embodiment, the present methods are used for screening of arterial aging and/or the presence of cardiovascular disease.

One skilled in the art will also appreciate the various causes for which a cardiovascular status of an individual may change. Examples include, but are not limited to, arterial aging, cardiovascular disease, interventions against cardiovascular disease risk or progression, medications or any combinations thereof. In one embodiment, the cardiovascular status of an individual is monitored because the individual has or is at risk for developing a cardiovascular disease. In general, an increase in the thickness of the intima layer and/or the intima to media thickness ratio indicates that the cardiovascular disease is progressing whereas a decrease in the thickness of the intima layer and/or the intima to media thickness ratio indicates that the cardiovascular disease is regressing.

EXAMPLE

The following example is illustrative of the present invention but are not meant to be limiting thereof.

The thickness of the combined carotid artery intima-media layers (IMT), estimated using 7-8 MHz frequency ultrasound, which measures the far artery wall, is a conventional technique for noninvasive assessment of the development of atherosclerosis. Increases in the IMT are positively associated with current and the future development of cardiovascular disease (CVD), but only weakly associated with the severity and extent of coronary heart disease (CHD), as assessed by angiography.

The aim of this example is to evaluate the usefulness and validity of a technique using high-frequency ultrasound for separately assessing the thickness of artery intima and media layers and evaluating the intima thickness and intima/media thickness ratio in 70-year-old subjects, with and without a history of CVD, who are participating in a health screening program (the PIVUS Study).

Subjects and Methods

One hundred consecutive subjects from a cohort of 1016 randomly selected persons, all aged 70 years, living in the Uppsala community and participating in the PIVUS (Prospective Investigation of the Vasculature in Uppsala Seniors) study are included in this evaluation. All individuals underwent a physical examination and recorded any medical history of CHD (myocardial infarction (MI), angina pectoris, coronary by-pass or balloon angioplasty), heart failure, stroke, hypertension, diabetes and hyperlipidemia. CVD is defined as the presence of CHD, heart failure, stroke or hypertension. CHD outcomes are defined by ICD-10 (International Classification of Diseases, 10th revision) codes I20-I25, stroke by ICD codes I60-I69, hypertension by ICD codes I10-I15, diabetes by ICD codes E10-E14 and hyperlipidemia by ICD code E78. The duration of hypertension, diabetes and hyperlipidemia is estimated as years of treatment for these disorders.

Measurements of Artery Wall Thickness

Before beginning the ultrasound imaging, individuals rest quietly for at least 15 minutes. Carotid total wall thickness and the thickness of the individual artery layers are assessed noninvasively using high-resolution ultrasonographic equipment (Osteoson® Minhorst GmbH, Meudt, Germany), fitted with a broad-banded probe with 25 MHz center frequency. The method is validated for the estimation of total artery wall thickness and media layer thickness in non-atherosclerotic superficial arteries in pigs. Briefly, the scan converter enables the image to be frozen at a selected scan-time (2 sec) and the unit permits two-dimensional data acquisition, presenting the results as scans A and B. About 128 lines of echo data are detected as an A-echo signal, sampled by an eight-bit analog-to-digital converter, converted by scanning to a rectangular format and viewed as B-mode images on a 32-colour scale monitor. Image resolution as defined by the product manual is approximately 0.07 mm axially along the ultrasonographic beam and the depth of focus is in the range of 13.5 to 14.5 mm in front of the tip of the probe. The system recognizes objects of about 0.015 mm in size, and the software-driven cursors permit a minimal digital display of 0.02 mm.

The left common carotid artery (LCCA) is examined at the point of the strongest pulse, in front of the sternocleidomastoid muscle, with the individuals sitting in an upright position and looking straight ahead. The three-layer image show the pulsating artery near wall and the artery lumen. Ten B scans (point estimates) are carried out and measurements of the thickness of the whole arterial wall and its layers are performed off-line. Means of the ten measurements are calculated and used in the analysis. The total thickness of the carotid wall is measured from the leading edge of the adventitia to the far edge of the intima. Measurements of the adventitia and intima are made using only the brightest echoes from leading edge to far edge, and the thickness of the media layer is measured as the distance between the two brightest echoes. The coefficient of variation (CV %), calculated from double estimates (based on the mean of 5 measurements each) in 20 subjects, is about 2.4% for total carotid wall thickness, about 4.2% for media thickness and about 8% for intima thickness. The values for artery wall layer given in this study are mean values based on 10 or more measurements. All ultrasonographic assessments are performed by the same investigator, who is blinded to the clinical data of the study subjects.

Statistical Methods

Comparison of numerical variables between groups is carried out using the 2-sample t-test or Wilcoxon Rank Sum test, depending on the result of the test for normality based on the Shapiro-Wilk W Test. The Chi square test is used to compare distributions of categorical variables. Spearman-rank correlation tests are used to investigate correlations between variables. The CV %, based on duplicate measurements, is estimated according to the formula: CV %=100×(SD/mean), and SD (standard deviation) is estimated as: $\sqrt{\Sigma d^2/2n}$, where d=difference between duplicate measurement values and n=number of duplicate determinations.

Results

The study group comprised 100 participants, 56 men and 44 women. The prevalence of cardiovascular disease is fairly similar in men and women. There is a tendency for a higher prevalence of diabetes mellitus in men than in women (10.7% vs 2%, respectively, P=0.08), Table 4.

TABLE 4

Distribution of cardiovascular diseases in the study group by gender

| | N | CVD* Yes N (%) No N (%) | CHD† Yes N (%) No N (%) | MI‡ Yes N (%) No N (%) | Stroke Yes N (%) No N (%) | Hypertension Yes N (%) No N (%) | Diabetes Yes N (%) No N (%) | Hyperlipidemia Yes N (%) No N (%) |
|---|---|---|---|---|---|---|---|---|
| Men | 56 | 21 (37.5%) 35 (62.5%) | 7 (12.5%) 49 (87.5%) | 5 (95%) 51 (91%) | 10 (18%) 45 (82%) | 17 (30.4%) 39 (69.6%) | 6 (10.7%) 50 (89.3%) | 12 (21.4%) 44 (79.6%) |
| Women | 44 | 18 (41%) 26 (59%) | 4 (9%) 40 (91%) | 2 (4.5%) 42 (95.5%) | 7 (16%) 37 (84%) | 13 (29.6%) 31 (70.4%) | 1 (2%) 43 (98%) | 9 (20.4%) 35 (79.6%) |
| P between groups§ | | 0.7 | 0.6 | 0.4 | 0.8 | 0.9 | 0.08 | 0.9 |
| Total | 100 | 39 (39%) | 11 (11%) | 7 (7%) | 17 (17%) | 30 (30%) | 7 (7%) | 21 (21%) |

*CVD: All cardiovascular diseases combined, including coronary heart disease (CHD), heart failure, stroke and hypertension
†CHD: including myocardial infarction, angina pectoris, coronary by-pass or ballon angioplasty
‡MI: myocardial infarction
§Chi square between groups In the whole study population (n=100), carotid intima thickness is positively associated with weight, body max index (BMI), waist circumference, hip circumference and waist/hip ratio (all P<0.005), as well as with duration of hypertension, duration of hyperlipidemia and number of cigarettes/week (all P<0.05). Intima thickness is also associated (borderline significance) with duration of smoking (r=0.19; P=0.057). The intima/media thickness ratio is positively associated with BMI, duration of hyperlipidemia and number of cigarettes/week (all P<0.05), Table 5. There are no significant associations between media thickness and risk factors for CVD. The thickness of the whole carotid wall is positively associated with weight, waist circumference and waist/hip ratio (all P<0.05), Table 5.

TABLE 5

Associations between risk factors for CVD and total carotid wall thickness, media thickness, intima thickness and intima/media ratio in the study group (n = 100)

| Parameter | total wall | | media | | intima | | intima/media | |
|---|---|---|---|---|---|---|---|---|
| | $r_s$ | P | $r_s$ | P | $r_s$ | P | $r_s$ | P |
| Weight | 0.26 | 0.01 | 0.09 | 0.6 | 0.36 | 0.0002 | 0.15 | 0.1 |
| BMI | 0.12 | 0.3 | −0.03 | 0.8 | 0.37 | 0.0001 | 0.24 | 0.02 |
| Waist | 0.21 | 0.03 | 0.05 | 0.5 | 0.38 | 0.0001 | 0.18 | 0.08 |
| Hip | 0.10 | 0.3 | −0.3 | 0.8 | 0.30 | 0.003 | 0.19 | 0.058 |
| waist/hip ratio | 0.29 | 0.003 | 0.18 | 0.08 | 0.31 | 0.0015 | 0.07 | 0.5 |
| duration of hypertension | −0.0002 | 0.9 | −0.02 | 0.8 | 0.27 | 0.006 | 0.13 | 0.2 |

TABLE 5-continued

Associations between risk factors for CVD and total carotid wall thickness, media thickness, intima thickness and intima/media ratio in the study group (n = 100)

| Parameter | total wall | | media | | intima | | intima/media | |
|---|---|---|---|---|---|---|---|---|
| | $r_s$ | P | $r_s$ | P | $r_s$ | P | $r_s$ | P |
| duration of hyperlipidemia | 0.06 | 0.6 | −0.17 | 0.1 | 0.39 | <0.0001 | 0.29 | 0.0037 |
| duration of smoking | −0.03 | 0.7 | −0.07 | 0.5 | 0.19 | 0.057 | 0.15 | 0.1 |
| number of cigarettes/week | −0.09 | 0.4 | −0.15 | 0.2 | 0.24 | 0.02 | 0.24 | 0.02 |

$r_s$ Spearman rank correlation coefficient

Compared with healthy subjects, subjects with a diagnosis of CVD, CHD, MI or stroke have a thinner mean carotid media layer (all P<0.05), a thicker intima layer (all P<0.0001) and a substantially (74% to 195%) higher intima/media thickness ratio (all P<0.0005), Table 2. Total artery wall thickness does not differ significantly in any of the CVD category groups from that in healthy subjects. Compared with healthy subjects, patients with hypertension or hyperlipidemia have thicker intima layers and a higher intima/media thickness ratio (P<0.0005 and P<0.05, respectively), Table 2. Separate analyses for men and women with regard to type of cardiovascular disease (Tables 6 and 7) reveal results fairly similar to those in the combined study group, Table 2. However, analysis by gender reveal that men have significantly higher mean values for carotid total wall thickness, media thickness and intima thickness than women (all P<0.05). Furthermore, men with diabetes mellitus have a thinner carotid media layer and men with hypertension have a thicker carotid intima layer than the equivalent layers in healthy men (P<0.05 for both), Table 6. The intima/media thickness ratio is also significantly higher in men with hypertension, diabetes or hyperlipidemia than in healthy men (all P<0.05), whereas no significant differences are found in women (Tables 6 and 7).

TABLE 6

Total carotid artery wall thickness, media thickness, intima thickness and intima/media thickness (I/M) ratio in men with varying types of CVD when compared with healthy men with no CVD (n = 35), Subjects with diabetes end hyperlipidemia were compared with subjects without these disorders

| Men n = 56 | total wall mean ± SD | P | media mean ± SD | P | intima mean ± SD | P | I/M ratio mean ± SD | P |
|---|---|---|---|---|---|---|---|---|
| All CVD* | | 0.5 | | <0.05 | | <0.0001 | | <0.001 |
| Yes (n = 21) | 0.77 ± 0.2 | | 0.41 ± 0.2 | | 0.24 ± 0.04 | | 0.71 ± 0.4 | |
| No (n = 35) | 0.81 ± 0.2 | | 0.49 ± 0.1 | | 0.18 ± 0.1 | | 0.40 ± 0.2 | |
| CHD† | | 0.07 | | <0.01 | | <0.005 | | <0.001 |
| Yes (n = 7) | 0.66 ± 0.3 | | 0.33 ± 0.1 | | 0.25 ± 0.03 | | 0.86 ± 0.3 | |
| No (n = 35) | 0.81 ± 0.2 | | 0.49 ± 0.1 | | 0.18 ± 0.07 | | 0.40 ± 0.2 | |
| MI‡ | | 0.4 | | <0.01 | | <0.01 | | <0.005 |
| Yes (n = 5) | 0.75 ± 0.2 | | 0.31 ± 0.1 | | 0.25 ± 0.03 | | 0.91 ± 0.3 | |
| No (n = 35) | 0.81 ± 0.2 | | 0.49 ± 0.1 | | 0.18 ± 0.1 | | 0.40 ± 0.2 | |
| Stroke | | 0.8 | | 0.2 | | <0.001 | | <0.01 |
| Yes (n = 10) | 0.83 ± 0.2 | | 0.42 ± 0.2 | | 0.26 ± 0.04 | | 0.79 ± 0.4 | |
| No (n = 35) | 0.81 ± 0.2 | | 0.49 ± 0.1 | | 0.18 ± 0.1 | | 0.40 ± 0.2 | |
| Hypertension | | 0.7 | | 0.2 | | <0.001 | | <0.01 |
| Yes (n = 17) | 0.77 ± 0.2 | | 0.43 ± 0.04 | | 0.24 ± 0.05 | | 0.65 ± 0.1 | |
| No (n = 35) | 0.81 ± 0.2 | | 0.49 ± 0.03 | | 0.18 ± 0.1 | | 0.40 ± 0.04 | |
| Diabetes | | 0.1 | | <0.05 | | 0.1 | | <0.05 |
| Yes (n = 6) | 0.72 ± 0.2 | | 0.32 ± 0.1 | | 0.23 ± 0.04 | | 0.80 ± 0.3 | |
| No (n = 50) | 0.80 ± 0.2 | | 0.43 ± 0.2 | | 0.20 ± 0.1 | | 0.48 ± 0.3 | |
| Hyperlipidemia | | 0.3 | | 0.4 | | <0.005 | | <0.05 |
| Yes§ (n = 12) | 0.85 ± 0.2 | | 0.43 ± 0.2 | | 0.25 ± 0.05 | | 0.71 ± 0.4 | |
| No (n = 44) | 0.78 ± 0.2 | | 0.47 ± 0.1 | | 0.19 ± 0.1 | | 0.47 ± 0.3 | |

*All CVD: All cardiovascular diseases combined, including coronary heart disease (CHD), heart failure, stroke and hypertension.
†CHD: including myocardial infarction, angina pectoris, coronary by-pass or ballon angioplasty
‡MI: myocardial infarction
§including subjects treated with lipid lowering medications

TABLE 7

Total carotid artery wall thickness, media thickness, intima thickness and intima/media thickness (I/M) ratio in women with varying types of CVD when compared with healthy women with no CVD (n = 26). Subjects with hyperlipidemia were compared with subjects without this disorder.

| Women n = 44 | total wall mean ± SD | P | media mean ± SD | P | intima mean ± SD | P | I/M ratio mean ± SD | P |
|---|---|---|---|---|---|---|---|---|
| *All CVD | | 0.6 | | 0.3 | | <0.01 | | 0.08 |
| Yes (n = 18) | 0.65 ± 0.2 | | 0.34 ± 0.2 | | 0.21 ± 0.01 | | 0.37 ± 0.6 | |
| No (n = 26) | 0.67 ± 0.1 | | 0.39 ± 0.1 | | 0.16 ± 0.01 | | 0.47 ± 0.2 | |

TABLE 7-continued

Total carotid artery wall thickness, media thickness, intima thickness and intima/media thickness (I/M) ratio in women with varying types of CVD when compared with healthy women with no CVD (n = 26). Subjects with hyperlipidemia were compared with subjects without this disorder.

| Women n = 44 | total wall mean ± SD | P | media mean ± SD | P | intima mean ± SD | P | I/M ratio mean ± SD | P |
|---|---|---|---|---|---|---|---|---|
| CHD† | | 0.3 | | <0.01 | | <0.0001 | | <0.005 |
| Yes (n = 4) | 0.62 ± 0.06 | | 0.19 ± 0.06 | | 0.27 ± 0.1 | | 1.60 ± 0.8 | |
| No (n = 26) | 0.67 ± 0.03 | | 0.39 ± 0.1 | | 0.16 ± 0.04 | | 0.47 ± 0.2 | |
| MI‡ | | 0.9 | | <0.05 | | <0.05 | | <0.05 |
| Yes (n = 2) | 0.66 ± 0.1 | | 0.15 ± 0.01 | | 0.33 ± 0.1 | | 2.18 ± 0.5 | |
| No (n = 26) | 0.66 ± 0.1 | | 0.38 ± 0.1 | | 0.17 ± 0.04 | | 0.52 ± 0.3 | |
| Stroke | | 0.5 | | 0.08 | | <0.0001 | | <0.005 |
| Yes (n = 7) | 0.63 ± 0.1 | | 0.29 ± 0.1 | | 0.23 ± 0.04 | | 0.84 ± 0.3 | |
| No (n = 26) | 0.67 ± 0.1 | | 0.39 ± 0.1 | | 0.16 ± 0.03 | | 0.47 ± 0.2 | |
| Hypertension | | 0.9 | | 0.9 | | 0.06 | | 0.8 |
| Yes (n = 13) | 0.67 ± 0.2 | | 0.38 ± 0.1 | | 0.19 ± 0.1 | | 0.58 ± 0.3 | |
| No (n = 26) | 0.67 ± 0.1 | | 0.39 ± 0.1 | | 0.16 ± 0.03 | | 0.47 ± 0.2 | |
| Hyperlipidemia | | 0.5 | | 0.2 | | <0.05 | | 0.08 |
| Yes§ | 0.65 ± 0.1 | | 0.32 ± 0.2 | | 0.22 ± 0.1 | | 0.95 ± 0.7 | |
| No | 0.67 ± 0.1 | | 0.38 ± 0.1 | | 0.17 ± 0.04 | | 0.51 ± 0.3 | |

*All CVD: All cardiovascular diseases combined, including coronary heart disease (CHD), heart failure, stroke and hypertension.
†CHD: including myocardial infarction, angina pectoris, coronary by-pass or ballon angioplasty
‡MI: myocardial infarction
§Including subjects treated with lipid lowering medications Discussion The main finding of this Example is that separate estimates of carotid intima thickness, media thickness, and the resulting intima/media thickness ratio, obtained noninvasively using high-frequency (25 MHz) ultrasound, result in highly significant differences between 70-year-old subjects with and without various forms of CVD. These findings are consistent and fairly similar in women and men. Thus, these findings indicate that separate estimates of intima and media thickness and the use of the intima/media thickness ratio could be a valuable tool in the evaluation of pathophysiological changes in the artery wall.

High-frequency ultrasound equipment can be reliably used to estimate total wall and media layer thickness, but is less suitable for estimation of intima layer thickness in non-atherosclerotic arteries. However, this study, which included subjects with atherosclerotic disease, indicates that assessing the intima thickness by itself results in clear, significant differentiation between subjects with and without atherosclerosis. Furthermore, subjects with a diagnosis of hypertension, stroke or hyperlipidemia also have thicker carotid intima layers than healthy subjects, suggesting additional potential value from estimation of the thickness of the intima layer using high-frequency ultrasound.

The conventional noninvasive assessment and monitoring of changes in the whole artery wall, i.e. the IMT, estimated using 7-8 MHz frequency ultrasound, has been widely used in epidemiological and clinical studies and has revealed acceptable associations with prevalence and risk of CVD. However, when Adams et al., "Carotid intima-media thickness is only weakly correlated with the extent and severity of coronary artery disease", *Circulation* 1995; 92(8):2127-34, compared IMT and coronary angiography in 350 subjects, the sensitivity and specificity of the technique for identifying patients with or without significant CHD are low. This could be explained by the fact that an increase in IMT is predominantly the result of an increase in the thickness of the intima layer. However, the thickness of the media layer is also included in the conventional IMT estimates. The simultaneous reduction in media thickness with increasing atherosclerosis will therefore diminish the sensitivity of the conventional IMT assessment. Furthermore, the specific changes in the thickness of the media layer cannot be identified by 7-8 MHz frequency ultrasonography because of the systematic overestimation of the intima layer and the systematic underestimation of the media layer associated with low resolution.

The clinical interpretation of low-resolution ultrasonography IMT measurements has been further questioned by Gamble et al, "B-mode ultrasound images of the carotid artery wall: correlation of ultrasound with histological measurements", *Atherosclerosis*, 1993; 102(2):163-73, who showed, by means of a validation study, that IMT measurements of carotid arteries (using 7-8 MHz frequency ultrasonography), in situ in cadavers best corresponded with histologically ascertained total artery wall thickness i.e. including adventitia, rather than with the intima+media complex per se. These findings may in part explain that values for the carotid intima plus media thickness in this Example are smaller than those from conventional IMT using 7-8 MHz frequency ultrasound. The values of this Example are, however, very similar to those obtained in men of similar age and in postmenopausal women using 10 MHz frequency ultrasound. As with the inventor's data, the IMT in men is significantly thicker than that in women when estimated using 7-8 MHz frequency ultrasound. Although sex differences in body fat distribution may account for part of this difference, the association between carotid IMT and waist/hip ratio is similar for both sexes.

A reduction in the thickness of the media layer of the carotid artery with aging, as well as in subjects with CVD or CHD, as indicated in this Example, may appear inconsistent with the abundant data of an increase in carotid IMT associated with the presence of CVD, as assessed by 7-8 MHz frequency probes. However, Gussenhoven et al., "Assessment of medial thinning in atherosclerosis by intravascular ultrasound", *Am. J. Cardiol.*, 1991; 68(17):1625-32, used high-frequency intravascular ultrasound to demonstrate that artery media thickness is reduced by atherosclerosis. The extent of medial thinning seems to be inversely related to the extent of intima thickening, indicating that medial thinning is an essential part of the atherosclerosis process. Morphometric studies in elderly subjects have also shown an age-related increase in intima and decrease in media thickness, particularly in the carotid arteries, as well as inverse correlations between media thickness and degree of stenosis in the aorta, and the carotid, coronary, and cerebral arteries.

The substantial difference in intima/media thickness ratio between subjects with CVD and healthy subjects found in this example clearly results from divergent changes in carotid intima and media thickness associated with arterial disease.

The inventor demonstrates substantial differences in the thicknesses of the artery intima and media layers between groups of subjects with and without CVD. The inventor suggests, therefore, that the use of noninvasive high-frequency ultrasound for separately estimating artery intima and media thickness is a valuable tool for assessing/monitoring changes caused by aging, atherosclerosis and the effects of medical interventions on the artery wall.

The specific embodiments and examples described herein are illustrious in nature only and are not intended to be limiting of the invention defined by the claims. Additional embodiments and examples of the various aspects of the invention defined by the claims and/or which are equivalent to the specific embodiments and examples set forth herein may be apparent to one of ordinary skill in the art and are included within the scope of the claimed invention.

What is claimed is:

1. A non-invasive method for evaluating artery wall status and risk of developing cardiovascular disease in an individual, comprising:
   (a) measuring a thickness of an artery intima layer in the individual and a thickness of an artery media layer in the individual using ultrasound employing a frequency greater than 15 MHz,
   (b) calculating a ratio of the measured intima thickness to the measured media thickness (measured I/M ratio), and
   (c) determining artery wall status and risk of developing cardiovascular disease in the individual by comparing the measured intima thickness and/or the measured I/M ratio to
      (i) a healthy intima thickness, comprising a mean intima thickness of a group of healthy subjects of the same sex and age of the individual, and/or a healthy I/M ratio, comprising a mean ratio of intima thickness to media thickness of a group of healthy subjects of the same sex and age of the individual, respectively, wherein if the measured intima thickness and/or the measured I/M ratio are greater than the healthy intima thickness and/or the healthy I/M ratio, respectively, the individual is evaluated as having an increased risk of cardiovascular disease, and
      (ii) an older intima thickness, comprising a mean intima thickness of a group of healthy subjects of the same sex of the individual and of a mean age greater than the age of the individual, and/or an older I/M ratio, comprising a mean ratio of intima thickness to media thickness of a group of healthy subjects of the same sex and of a mean age greater than the age of the individual, respectively, wherein if the measured intima thickness and/or the measured I/M ratio are equivalent to or greater than the older intima thickness and/or the older I/M ratio, respectively, the individual is evaluated as having an increased risk of cardiovascular disease.

2. The method of claim 1, wherein the measuring step is performed in a superficial artery of the individual.

3. The method of claim 2, wherein the superficial artery comprises a carotid artery, a femoral artery, a radialis artery, a cubital artery, a temporal artery, a popliteal artery, a dorsalis pedis artery or the measuring step is performed in a combination of arteries.

4. The method of claim 1, wherein the cardiovascular disease comprises coronary heart disease, heart failure, or stroke.

5. The method of claim 1, wherein the cardiovascular disease comprises coronary heart disease.

6. The method of claim 1, wherein the cardiovascular disease comprises myocardial infarction.

7. The method of claim 1, wherein the cardiovascular disease comprises stroke.

8. The method of claim 1, wherein the cardiovascular disease comprises heart failure.

9. The method of claim 1, wherein the measured intima thickness and/or the measured I/M ratio are also compared with a diseased intima thickness comprising a mean intima thickness of a group of subjects of the same sex and age of the individual and having cardiovascular disease, and/or a diseased I/M ratio comprising a mean ratio of intima thickness to media thickness of a group of subjects of the same sex and age of the individual and having cardiovascular disease, respectively, wherein if the measured intima thickness and/or the measured I/M ratio are equivalent to or greater than the diseased intima thickness and/or the diseased I/M ratio, respectively, the individual is evaluated as having an increased risk of cardiovascular disease.

10. The method of claim 9, wherein the measured I/M ratio is compared with the diseased I/M ratio, and the diseased I/M ratio is greater than or equal to about 0.52.

11. The method of claim 9, wherein the measured intima thickness is compared with the diseased intima thickness, and the diseased intima thickness is greater than or equal to about 0.19 mm.

12. A non-invasive method for evaluating artery wall status and risk of developing cardiovascular disease selected from the group consisting of coronary heart disease, heart failure, and stroke in an individual, comprising:
   (a) measuring a thickness of an artery intima layer in the individual and a thickness of an artery media layer in the individual using ultrasound employing a frequency greater than 15 MHz,
   (b) calculating a ratio of the measured intima thickness to the measured media thickness (measured I/M ratio), and
   (c) determining artery wall status and risk of developing cardiovascular disease in the individual by comparing the measured intima thickness and/or measured I/M ratio to
      an older intima thickness, comprising a mean intima thickness of a group of healthy subjects of the same sex of the individual and of a mean age greater than the age of the individual, and/or an older I/M ratio, comprising a mean ratio of intima thickness to media thickness of a group of healthy subjects of the same sex and of a mean age greater than the age of the individual, respectively, wherein if the measured intima thickness and/or the measured I/M ratio are equivalent to or greater than the older intima thickness and/or the older I/M ratio, respectively, the individual is evaluated as having an increased risk of said cardiovascular disease,
   wherein the method optionally includes the additional step (ii) and/or step (iii)
      (ii) comparing the measured intima thickness and/or measured I/M ratio to a healthy intima thickness, comprising a mean intima thickness of a group of healthy subjects of the same sex and age of the individual, and/or a healthy I/M ratio, comprising a mean ratio of intima thickness to media thickness of a group of healthy subjects of the same sex and age of the individual, respectively, wherein if the measured intima thickness and/or the measured I/M ratio are greater than the healthy intima thickness and/or the healthy I/M ratio, respectively, the individual is evaluated as having an increased risk of cardiovascular disease, (iii) comparing the measured intima thickness and/or measured I/M ratio to a diseased intima thickness comprising a mean intima thickness of a group of subjects of the same sex and age of the individual and having said cardiovascular disease, and/or a diseased I/M ratio, comprising a mean ratio of intima thickness to media thickness of a group of subjects of the same sex and age of the individual and having cardiovascular disease, respectively, wherein if the measured intima thickness and/or the measured I/M ratio are equivalent to or greater than the diseased intima thickness and/or the diseased I/M ratio, respectively, the individual is evaluated as having an increased risk of said cardiovascular disease.

13. The method of claim 12, wherein the measuring step is performed in a superficial artery of the individual.

14. The method of claim 13, wherein the superficial artery comprises a carotid artery, a femoral artery, a radialis artery, a cubital artery, a temporal artery, a popliteal artery, a dorsalis pedis artery or measuring step is performed in a combination of arteries.

15. The method of claim 12, wherein the measured I/M ratio is compared with the diseased I/M ratio, and the diseased I/M ratio is greater than or equal to about 0.52.

16. The method of claim 12, wherein the measured intima thickness is compared with the diseased intima thickness, and the diseased intima thickness is greater than or equal to about 0.19 mm.

17. The method of claim 12, wherein the cardiovascular disease comprises coronary heart disease.

18. The method of claim 12, wherein the cardiovascular disease comprises myocardial infarction.

19. The method of claim 12, wherein the cardiovascular disease comprises heart failure.

20. The method of claim 12, wherein the cardiovascular disease comprises stroke.

21. The method of claim 12, wherein the measured intima thickness and the measured I/M ratio are compared with the healthy intima thickness and the healthy I/M ratio, respectively, with the older intima thickness and the older I/M ratio, respectively, and with the diseased intima thickness and the diseased I/M ratio, respectively.

* * * * *